United States Patent
Sugimoto

(10) Patent No.: US 10,710,946 B2
(45) Date of Patent: Jul. 14, 2020

(54) METHOD OF MANUFACTURING OCTAFLUOROCYCLOPENTENE

(71) Applicant: ZEON CORPORATION, Chiyoda-ku, Tokyo (JP)

(72) Inventor: Tatsuya Sugimoto, Tokyo (JP)

(73) Assignee: ZEON CORPORATION, Chiyoda-ku, Tokyo (JP)

(*) Notice: Subject to any disclaimer, the term of this patent is extended or adjusted under 35 U.S.C. 154(b) by 0 days.

(21) Appl. No.: 16/612,759

(22) PCT Filed: Jun. 1, 2018

(86) PCT No.: PCT/JP2018/021235
§ 371 (c)(1),
(2) Date: Nov. 12, 2019

(87) PCT Pub. No.: WO2018/235567
PCT Pub. Date: Dec. 27, 2018

(65) Prior Publication Data
US 2020/0181046 A1    Jun. 11, 2020

(30) Foreign Application Priority Data
Jun. 22, 2017 (JP) .................. 2017-122358

(51) Int. Cl.
*C07C 17/20* (2006.01)
*C07C 23/08* (2006.01)

(52) U.S. Cl.
CPC ............ *C07C 17/204* (2013.01); *C07C 17/20* (2013.01); *C07C 23/08* (2013.01)

(58) Field of Classification Search
CPC ................... C07C 17/20; C07C 23/08
See application file for complete search history.

(56) References Cited

U.S. PATENT DOCUMENTS 3,567,788 A    3/1971   Carr et al.
6,211,420 B1   4/2001   Sekiya et al.

FOREIGN PATENT DOCUMENTS

| JP | H0995458 A   | 4/1997 |
| JP | 2001240568 A | 9/2001 |
| JP | 2001247493 A | 9/2001 |
| JP | 2001261594 A | 9/2001 |
| JP | 2006151998 A | 6/2006 |
| WO | 9743233 A1   | 11/1997 |

OTHER PUBLICATIONS

Dec. 24, 2019, International Preliminary Report on Patentability issued in the International Patent Application No. PCT/JP2018/021235.

John T. Maynard, The Synthesis of Highly Fluorinated Compounds by Use of Potassium Fluoride in Polar Solvents, The Journal of Organic Chemistry, Jan. 1, 1963, pp. 112-115, vol. 28.

*Primary Examiner* — Jafar F Parsa
(74) *Attorney, Agent, or Firm* — Kenja IP Law PC

(57) ABSTRACT

Provided is a manufacturing method in which 1-chloroheptafluorocyclopentene is brought into contact with an alkali metal fluoride to obtain octafluorocyclopentene. The manufacturing method includes a fluorination step of maintaining, at 85° C. or higher, a suspension containing an alkali metal fluoride suspended in a mixed solvent including a polar aprotic solvent and a glycol ether having a higher boiling point than the polar aprotic solvent while supplying 1-chloroheptafluoropentene into the suspension and performing fluorination thereof to obtain octafluorocyclopentene.

5 Claims, No Drawings

METHOD OF MANUFACTURING OCTAFLUOROCYCLOPENTENE

TECHNICAL FIELD

The present disclosure relates to a method of manufacturing octafluorocyclopentene. In particular, the present disclosure relates to a manufacturing method in which 1,2,3,3,4,4,5,5-octafluorocyclopentene is manufactured through fluorination of 1-chloroheptafluorocyclopentene.

BACKGROUND 1,2,3,3,4,4,5,5-Octafluorocyclopentene (hereinafter, also referred to as "octafluorocyclopentene") is useful as a gas for plasma reaction in etching, chemical vapor deposition (CVD), and so forth that may be performed in a manufacturing step of a semiconductor device or as a feedstock for a fluorine-containing pharmaceutical intermediate, a photochromic molecule material, or the like. Highly purified octafluorocyclopentene, in particular, can suitably be used as a plasma etching gas, CVD gas, or the like that can be used in a manufacturing step of a semiconductor device.

A number of methods of manufacturing octafluorocyclopentene have been proposed in recent years. For example, Patent Literature (PTL) 1 discloses that octafluorocyclopentene was obtained in a yield of 93.1% by using potassium fluoride to perform fluorination in N,N-dimethylformamide solvent with respect to a mixture of compounds including at least two chlorine atoms that contained 1,2-dichlorohexafluorocyclopentene, 1,2,3-trichloroheptafluorocyclopentene, and 1,2,3,5-tetrachlorotetrafluorocyclopentene. The mixture was obtained through fluorination of hexachlorocyclopentadiene by anhydrous hydrogen fluoride.

PTL 2 discloses that octafluorocyclopentene was obtained in a yield of 87.8% using 1,2-dichlorohexafluorocyclopentene as a feedstock by carrying out a reaction in N,N-dimethylformamide solvent using potassium fluoride as a fluorinating agent while adjusting the dripping rate of the feedstock and the withdrawal rate of octafluorocyclopentene (product).

PTL 3 discloses that octafluorocyclopentene was obtained in a yield of 90% by using potassium fluoride to perform fluorination of a mixture containing 1-chloroheptafluorocyclopentene, 1,2-dichlorohexafluorocyclopentene, trichloropentafluorocyclopentene, tetrachlorotetrafluorocyclopentene, and pentachlorotrifluorocyclopentene that was obtained through gas phase fluorination by anhydrous hydrogen fluoride using octachlorocyclopentene as a starting material.

PTL 4 discloses that octafluorocyclopentene was obtained in a yield of 87% by using potassium fluoride to fluorinate a feedstock having 1-chloroheptafluorocyclopentene as a main component in N,N-dimethylformamide solvent.

PTL 5 discloses that octafluorocyclopentene was obtained in a yield of 72% using 1-chloroheptafluorocyclopentene as a feedstock by performing heating under reflux in a mixed solvent of N,N-dimethylformamide and benzene, which is a non-polar solvent, with potassium fluoride as a fluorinating agent.

Non-Patent Literature (NPL) 1 discloses that octafluorocyclopentene was obtained in a yield of 72% using octachlorocyclopentene as a feedstock by performing fluorination in N-methylpyrrolidone solvent with potassium fluoride as a fluorinating agent.

CITATION LIST

Patent Literature

PTL 1: WO 1997/043233 A1
PTL 2: JP H9-95458 A
PTL 3: JP 2006-151998 A
PTL 4: JP 2001-247493 A
PTL 5: U.S. Pat. No. 3,567,788 A

Non-Patent Literature

NPL 1: John T. Maynard, Journal of Organic Chemistry, 1963, vol. 28, p. 112-115

SUMMARY

Technical Problem

With regards to methods of manufacturing octafluorocyclopentene that can suitably be used in applications such as described above, there has been increasing need for higher yield in recent years. However, it has not been possible to sufficiently increase the yield of octafluorocyclopentene in various manufacturing methods that have previously been proposed, such as those described above.

Accordingly, an objective of the present disclosure is to provide a manufacturing method that can sufficiently increase the yield of octafluorocyclopentene.

Solution to Problem

In view of the above, the inventor firstly focused on a fluorination step in which 1-chloroheptafluorocyclopentene is brought into contact with an alkali metal fluoride in order to fluorinate the 1-chloroheptafluorocyclopentene. More specifically, the inventor attempted to carry out this fluorination step by supplying a feedstock of 1-chloroheptafluorocyclopentene into a reactor while reacting the 1-chloroheptafluorocyclopentene with an alkali metal fluoride serving as a fluorinating agent and removing the obtained octafluorocyclopentene from the reactor in accordance with a method described in PTL 2 or PTL 3. As a result, the inventor found that when 1-chloroheptafluorocyclopentene is continuously supplied into the reactor as a feedstock, the temperature of the inside of the reactor (reaction contents) tends to gradually decrease. In more detail, the inventor determined that the rate of conversion of carbon-chlorine bonds to carbon-fluorine bonds slows significantly when the internal temperature drops below approximately 85° C., and that this leads to reduction of the yield of octafluorocyclopentene, which is the target product.

The inventor presumed that one factor causing the temperature in the reaction of 1-chloroheptafluorocyclopentene and the alkali metal fluoride inside the reaction vessel (i.e., the internal temperature) to decrease is the fact that 1-chloroheptafluorocyclopentene has a low boiling point of 56° C. Note that 1,2-dichlorohexafluorocyclopentene used as a feedstock in PTL 1 and 2, for example, has a boiling point of 90° C., whereas compounds having more chlorine atoms than 1,2-dichlorohexafluorocyclopentene have a boiling point of even higher than 90° C. Also note that a mixture containing two or more of such compounds also has a boiling point of higher than 90° C. Therefore, when a fluorination step carried out in a liquid phase such as disclosed in PTL 1 and 2 is envisaged, it is thought that in a case in which a feedstock of 1-chloroheptafluorocyclopentene is brought into contact with a suspension of a reaction solvent and an alkali metal fluoride, the influence of heat of vaporization and the like will be large and the effect of lowering the internal temperature will be large compared to a case in which 1,2-dichlorohexafluorocyclopentene is used as a feedstock, as in a conventional method. As previously described, if the internal temperature decreases, the rate of the fluorination reaction in the fluorination step slows significantly, and this leads to a large amount of unreacted 1-chloroheptafluorocyclopentene remaining in the reaction system and thus tending to be removed from the reactor together with octafluorocyclopentene, which is the target product. As a consequence, the yield of octafluorocyclopentene may decrease.

One strategy that may be considered for inhibiting reduction of the rate of the fluorination reaction caused by reduction of internal temperature is to slow the rate at which 1-chloroheptafluorocyclopentene is supplied into the reactor as a feedstock. However, this is not a realistic strategy because slowing the feedstock supply rate significantly increases the time required for the fluorination step, which may lead to lower productivity.

Another strategy would be to raise an initial setting for the internal temperature. However, it is expected that when 1-chloroheptafluorocyclopentene is supplied into the reactor as a feedstock, the internal temperature will still decrease due to the low boiling point of 1-chloroheptafluorocyclopentene as previously described, and thus the yield of octafluorocyclopentene will decrease.

Yet another strategy would be to adjust the internal temperature through heating of the reactor during the fluorination step. However, this strategy is unrealistic because it is extremely difficult to perform control such that the heating temperature of the reactor is adjusted in accordance with variation of the internal temperature in order that the internal temperature is constantly at a desired value.

In light of the circumstances set forth above, the inventor reached a new discovery that reduction of internal temperature can be effectively inhibited by carrying out the fluorination step in a liquid phase containing a mixed solvent of a polar aprotic solvent and a solvent having particular attributes, and in this manner completed the present disclosure.

The present disclosure aims to advantageously solve the problems set forth above by disclosing a method of manufacturing octafluorocyclopentene by bringing 1-choroheptafluorocyclopentene into contact with an alkali metal fluoride to obtain octafluorocyclopentene, comprising: a fluorination step of maintaining, at 85° C. or higher, a suspension containing the alkali metal fluoride suspended in a mixed solvent including a polar aprotic solvent and a glycol ether having a higher boiling point than the polar aprotic solvent while supplying 1-chloroheptafluoropentene into the suspension and performing fluorination thereof to obtain octafluorocyclopentene; and a recovery step of recovering the octafluorocyclopentene that is produced in the fluorination step. This manufacturing method can sufficiently increase the yield of octafluorocyclopentene.

Note that the "boiling point" of various solvents referred to in the present specification is the boiling point at 1 atmosphere.

In the presently disclosed method of manufacturing octafluorocyclopentene, a volume proportion of the glycol ether in the mixed solvent is preferably not less than 10 volume % and not more than 30 volume % relative to 100 volume % of the polar aprotic solvent. When the volume proportion of the glycol ether in the mixed solvent is not less than 10 volume % and not more than 30 volume % relative to 100 volume % of the polar aprotic solvent, the yield of octafluorocyclopentene can be further improved, and a fluorination reaction can be promoted in the fluorination step.

Note that the "volume proportion" referred to in the present specification is the volume proportion at 23° C.

In the presently disclosed method of manufacturing octafluorocyclopentene, the polar aprotic solvent is preferably N,N-dimethylformamide or N,N-dimethylacetamide. When the polar aprotic solvent is N,N-dimethylformamide or N,N-dimethylacetamide, the yield of octafluorocyclopentene can be further increased.

In the presently disclosed method of manufacturing octafluorocyclopentene, the glycol ether is preferably a dialkyl ether of polyethylene glycol or a dialkyl ether of polypropylene glycol. When the glycol ether is a dialkyl ether of polyethylene glycol or a dialkyl ether of polypropylene glycol, reduction of the temperature of the suspension during the fluorination step can be effectively inhibited, and the manufacturing efficiency and yield of octafluorocyclopentene can be further increased.

In the presently disclosed method of manufacturing octafluorocyclopentene, the glycol ether preferably includes at least one of diethylene glycol dimethyl ether, diethylene glycol diethyl ether, triethylene glycol dimethyl ether, tetraethylene glycol dimethyl ether, and dipropylene glycol dimethyl ether. When the glycol ether includes any of those listed above, reduction of the temperature of the suspension during the fluorination step can be effectively inhibited, and the manufacturing efficiency and yield of octafluorocyclopentene can be further increased.

DETAILED DESCRIPTION

The following provides a detailed description of embodiments of the present disclosure. The presently disclosed method of manufacturing octafluorocyclopentene (hereinafter, also referred to simply as the "presently disclosed manufacturing method", etc.) can suitably be implemented without any specific limitations in a known manufacturing apparatus that includes a reactor and a distillation column or a rectification column.

The presently disclosed manufacturing method includes: a fluorination step of maintaining, at 85° C. or higher, a suspension containing an alkali metal fluoride suspended in a mixed solvent including a polar aprotic solvent and a glycol ether having a higher boiling point than the polar aprotic solvent while supplying 1-chloroheptafluoropentene into the suspension and performing fluorination thereof to obtain octafluorocyclopentene; and a recovery step of recovering octafluorocyclopentene that is produced in the fluorination step.

The presently disclosed manufacturing method enables the manufacture of octafluorocyclopentene in a high yield as a result of the fluorination step being implemented using an alkali metal fluoride suspension that is prepared using a mixed solvent including a polar aprotic solvent and a glycol ether having a higher boiling point than the polar aprotic solvent. The presently disclosed manufacturing method may further include a preparation step at an earlier stage than the fluorination step.

The following provides a detailed description of various elements such as a feedstock, a mixed solvent, and an alkali metal fluoride that can be used in the presently disclosed manufacturing method and then describes an example of various steps that can be included in the presently disclosed manufacturing method.

[Feedstock]

In the presently disclosed manufacturing method, 1-chloroheptafluorocyclopentene is used as a feedstock. The 1-chloroheptafluorocyclopentene may be prepared according to a known method. For example, U.S. Pat. No. 3,567,788 A discloses that 1-chloroheptafluorocyclopentene was obtained in a yield of 74% by fluorinating 1,2-dichlorohexafluorocyclopentene in dimethyl sulfoxide solvent using anhydrous potassium fluoride. Moreover, J P 2001-240568 A discloses that 1-chloroheptafluorocyclopentene was obtained in a maximum yield of 89.1% by using potassium fluoride to fluorinate a feedstock of polychlorofluorocyclopentene (1,2-dichlorohexafluorocyclopentene, 1,2,3-trichloropentafluorocyclopentene, 1,2,4-trichloropentafluorocyclopentene, 1,2,3,4-tetrachlorotetrafluorocyclopentene, 1,2,3,3,4-pentachlorotrifluorocyclopentene, etc.) in a mixed solvent of N,N-dimethylformamide and an aromatic hydrocarbon such as toluene.

Furthermore, J P 2001-261594 A discloses that 1-chloroheptafluorocyclopentene was obtained in a maximum yield of 95.6% using 1,1-dichlorooctafluorocyclopentane as a feedstock by performing hydrogen reduction in the presence of a palladium alloy catalyst having a transition metal such as copper, tin, or bismuth as a main component.

[Mixed Solvent]

The mixed solvent used in the presently disclosed manufacturing method includes a polar aprotic solvent and a glycol ether having a higher boiling point than the polar aprotic solvent. The use of a mixed solvent that is obtained through mixing of a polar aprotic solvent and a glycol ether having a higher boiling point than the polar aprotic solvent can effectively inhibit reduction of the temperature of the suspension during the fluorination step. Note that in a case in which 1-chloroheptafluorocyclopentene used as a feedstock is brought into contact with an alkali metal fluoride serving as a fluorinating agent and is fluorinated in a liquid phase, the rate of the fluorination reaction decreases if the temperature of the suspension in which the fluorinating agent is suspended decreases. A decrease in the rate of the fluorination reaction leads to an increase in the ratio of unreacted feedstock present in the reaction system. This makes it easier for unreacted feedstock to vaporize without undergoing fluorination, move into a recovery mechanism such as a rectification column, and be recovered together with reaction product obtained through the fluorination step. Therefore, by setting the composition of the mixed solvent used in the presently disclosed manufacturing method as described above, reduction of the temperature of the suspension in the fluorination step can be effectively inhibited, reduction of the reaction rate in the fluorination step can be inhibited, and 1-chloroheptafluorocyclopentene can be efficiently fluorinated to produce octafluorocyclopentene. Accordingly, the presently disclosed manufacturing method including this fluorination step enables production of octafluorocyclopentene in a high yield and increased manufacturing efficiency through the inhibitive effect on reduction of the reaction rate. It should be noted that the mixed solvent may include a third solvent that is a solvent other than the polar aprotic solvent and the glycol ether having a higher boiling point than the polar aprotic solvent. —Polar Aprotic Solvent—

Amide solvents can suitably be used as the polar aprotic solvent. Examples of amide solvents that can be used include, but are not specifically limited to, N-methylformamide (boiling point: 197° C.), N,N-dimethylformamide (boiling point: 153° C.), N,N-diethylformamide (boiling point: 177° C.), acetamide (boiling point: 222° C.), N,N-dimethylacetamide (boiling point: 165° C.), N,N-diethylacetamide (boiling point: 185° C.), N-methylpyrrolidone (boiling point: 202° C.), and N,N-dimethylimidazolidinone (boiling point: 225° C.). Of these amide solvents, linear amide solvents such as N-methylformamide, N,N-dimethylformamide, N,N-diethylformamide, acetamide, N,N-dimethylacetamide, and N,N-diethylacetamide are preferable in view that they can further increase the yield of octafluorocyclopentene, and N,N-dimethylformamide and N,N-dimethylacetamide, the industrial acquisition of which is particularly easy, are more preferable. Although one polar aprotic solvent may be used individually or two or more polar aprotic solvents may be used in combination, it is preferable that one polar aprotic solvent is used individually since this facilitates charging during implementation of the presently disclosed manufacturing method.

Note that in a case in which the polar aprotic solvent is a mixture of two or more solvents, the proportion constituted by one solvent that is a main component of the polar aprotic solvent mixture (i.e., the "main polar aprotic solvent") is preferably more than 50 volume %, more preferably more than 80 volume %, and particularly preferably more than 90 volume % when the entire mixture is taken to be 100 volume %. Moreover, in a case in which the polar aprotic solvent is a mixture of two or more solvents, the boiling point of the glycol ether that is used therewith is required to be higher than the boiling point of at least the main polar aprotic solvent. Furthermore, in a case in which the mixed solvent used in the presently disclosed manufacturing method includes two or more types of glycol ethers, the proportion constituted by one glycol ether that is a main component of the glycol ethers (i.e., the "main glycol ether") is preferably more than 50 volume %, more preferably more than 80 volume %, and particularly preferably more than 90 volume % when all of the glycol ethers are taken to be 100 volume %. Also note that at least the boiling point of the main glycol ether is required to be higher than the boiling point of the main polar aprotic solvent.

The boiling point of the polar aprotic solvent is preferably 140° C. or higher, and is preferably 150° C. or higher. When the boiling point of the polar aprotic solvent is not lower than any of the lower limits set forth above, the yield of octafluorocyclopentene can be more sufficiently increased, and the manufacturing efficiency of octafluorocyclopentene can be increased.

The amount of the polar aprotic solvent that is used per 1 g of 1-chloroheptafluorocyclopentene used as a feedstock is preferably 1.0 mL or more, and more preferably 1.2 mL or more, and is preferably 1.5 mL or less. When the amount of the polar aprotic solvent that is used is not less than any of the lower limits set forth above, the viscosity of the suspension does not increase excessively, ease of stirring increases in stirring for bringing 1-chloroheptafluorocyclopentene and the alkali metal fluoride into contact in the liquid phase during the fluorination step, and the efficiency of contacting thereof is further improved, which enables higher fluorination reaction efficiency in the fluorination step. Moreover, the use of an amount of polar aprotic solvent that is not more than the upper limit set forth above is financially beneficial in industry. —Glycol Ether—

The glycol ether is a compound having a higher boiling point than the polar aprotic solvent used therewith. Examples of glycol ethers that can be used include, but are not specifically limited to, dialkyl ethers of polyethylene glycol and dialkyl ethers of polypropylene glycol. When the glycol ether is a dialkyl ether of polyethylene glycol or a dialkyl ether of polypropylene glycol, reduction of the temperature of the suspension during the fluorination step can be effectively inhibited, and the manufacturing efficiency and yield of octafluorocyclopentene can be further increased. Note that the dialkyl ether of polyethylene glycol preferably has an alkyl group carbon number of 4 or less. Moreover, the dialkyl ether of polypropylene glycol preferably has an alkyl group carbon number of 2 or less. Specific examples of dialkyl ethers of polyethylene glycol that can be used include diethylene glycol dimethyl ether (boiling point: 162° C.), diethylene glycol diethyl ether (boiling point: 188° C.), diethylene glycol ethyl methyl ether (boiling point: 179° C.), diethylene glycol dibutyl ether (boiling point: 255° C.), triethylene glycol dimethyl ether (boiling point: 216° C.), triethylene glycol diethyl ether (boiling point: >216° C.), tetraethylene glycol dimethyl ether (boiling point: 276° C.), and tetraethylene glycol diethyl ether (boiling point: >276° C.). Specific examples of dialkyl ethers of polypropylene glycol that can be used include dipropylene glycol dimethyl ether (boiling point: 175° C.), dipropylene glycol diethyl ether (boiling point: >175° C.), and tripropylene glycol dimethyl ether (boiling point: >241° C.). Although one glycol ether may be used individually or two or more glycol ethers may be used in combination, it is preferable that one glycol ether is used individually since this facilitates charging during implementation of the presently disclosed manufacturing method.

Of these glycol ethers, diethylene glycol dimethyl ether, diethylene glycol diethyl ether, triethylene glycol dimethyl ether, tetraethylene glycol dimethyl ether, and dipropylene glycol dimethyl ether are more preferable in terms of being easily industrially acquirable. When the glycol ether includes any of those listed above, reduction of the temperature of the suspension during the fluorination step can be effectively inhibited, and the manufacturing efficiency and yield of octafluorocyclopentene can be further increased.

The boiling point of the glycol ether is preferably 150° C. or higher, and is preferably 160° C. or higher. Moreover, the boiling point of the glycol ether is preferably at least 5° C. higher, and more preferably at least 7° C. higher than the boiling point of the polar aprotic solvent used therewith. When the boiling point of the glycol ether is not less than any of the lower limits set forth above and/or the difference between the boiling point of the glycol ether and the boiling point of the polar aprotic solvent is not less than any of the lower limits set forth above, reduction of the temperature of the suspension in the fluorination step can be effectively inhibited, the yield of octafluorocyclopentene can be more sufficiently increased, and the manufacturing efficiency of octafluorocyclopentene can be increased. The upper limit for the difference between the boiling point of the glycol ether and the boiling point of the polar aprotic solvent may be 200° C. or less, but is not specifically limited thereto.

The volume proportion of the glycol ether in the mixed solvent relative to 100 volume % of all polar aprotic solvent included in the mixed solvent is preferably 10 volume % or more, and more preferably 15 volume % or more, and is preferably 30 volume % or less, and more preferably 25 volume % or less. When the volume proportion of the glycol ether is not less than any of the lower limits set forth above, the effect of inhibiting reduction of the temperature of the suspension in the fluorination step can be better displayed, and the yield of octafluorocyclopentene can be further improved. Moreover, when the volume proportion of the glycol ether is not more than any of the upper limits set forth above, the alkali metal fluoride can dissolve in the polar aprotic solvent in an amount that can promote fluorination reaction in the fluorination step. Note that in a case in which the mixed solvent contains two or more polar aprotic solvents and/or two or more glycol ethers, it is preferable that the volume proportion set forth above is satisfied by the total content of polar aprotic solvents and the total content of glycol ethers.

As described above, the mixed solvent used in the fluorination step of the presently disclosed manufacturing method is required to include a polar aprotic solvent and a glycol ether having a higher boiling point than the polar aprotic solvent. Examples of combinations of a polar aprotic solvent and a glycol ether that can be used include, but are not specifically limited to, N,N-dimethylformamide/diethylene glycol dimethyl ether, N,N-dimethylformamide/diethylene glycol diethyl ether, N,N-dimethylformamide/triethylene glycol dimethyl ether, N,N-dimethylformamide/tetraethylene glycol dimethyl ether, N,N-dimethylformamide/dipropylene glycol dimethyl ether, N,N-dimethylacetamide/diethylene glycol diethyl ether, N,N-dimethylacetamide/triethylene glycol dimethyl ether, N,N-dimethylacetamide/tetraethylene glycol dimethyl ether, and N,N-dimethylacetamide/dipropylene glycol dimethyl ether. Of these combinations, N,N-dimethylformamide/triethylene glycol dimethyl ether, N,N-dimethylformamide/tetraethylene glycol dimethyl ether, N,N-dimethylacetamide/triethylene glycol dimethyl ether, N,N-dimethylacetamide/tetraethylene glycol dimethyl ether, and N,N-dimethylacetamide/dipropylene glycol dimethyl ether are preferable from a viewpoint of reactivity.

It is preferable that the polar aprotic solvent and the glycol ether used in preparation of the mixed solvent have undergone a drying process in advance. The drying can be carried out by a standard method without any specific limitations. For example, a method in which a desiccant is added to the used polar aprotic solvent/glycol ether and is left therewith for a certain time and/or a method in which the polar aprotic solvent/glycol ether is passed through a column packed with a desiccant and is recovered may be adopted.

[Alkali Metal Fluoride]

Some of the alkali metal fluoride is dissolved in the mixed solvent having a composition such as described above and the remaining alkali metal fluoride is dispersed in the mixed solvent so as to form a suspension. The alkali metal fluoride in the suspension functions as a fluorinating agent for the feedstock in the presently disclosed manufacturing method. Examples of alkali metal fluorides that can be used include potassium fluoride and cesium fluoride. Of these alkali metal fluorides, potassium fluoride is suitable for use because of its low industrial cost. One of these alkali metal fluorides may be used individually, or two or more of these alkali metal fluorides may be used in combination. With regards to the form of the alkali metal fluoride, a powdered form that has been dried as thoroughly as possible is preferable from a viewpoint of reactivity, and a spray dried product is more preferable. A spray dried product of an alkali metal fluoride tends to have a large specific surface area and has excellent dispersibility compared to an alkali metal fluoride of a typical commercially available product that has not undergone spray drying.

The amount of the alkali metal fluoride that is used is preferably within a range of 1.0 molar equivalents to 2.0 molar equivalents, and more preferably within a range of 1.1 molar equivalents to 1.5 molar equivalents relative to 1-chloroheptafluorocyclopentene used as a feedstock. When the amount of the alkali metal fluoride that is used is not less than any of the lower limits set forth above, it is possible to sufficiently inhibit unreacted 1-chloroheptafluorocyclopentene from remaining in the fluorination step and further improve the yield of octafluorocyclopentene. Moreover, when the amount of the alkali metal fluoride that is used is not more than any of the upper limits set forth above, it is possible to prevent the amount of solid content inside the reactor after the fluorination reaction becoming excessively large and facilitate discharge of solid content from the inside of the reactor.

The following describes an example of various steps that may be included in the presently disclosed manufacturing method. An example of a manufacturing apparatus that can suitably implement the presently disclosed manufacturing method is an apparatus that includes a rectification column installed at the top of a reactor equipped with a stirrer and a feedstock supply pump. A receiver for trapping octafluorocyclopentene obtained as a reaction product may be installed at a withdrawal port of the rectification column. Moreover, a condenser for performing refluxing may be installed at the top of the rectification column and a coolant having a temperature within a range of −20° C. to 0° C. may be circulated. The following describes an example of the various steps for a case in which the presently disclosed manufacturing method is implemented by a manufacturing apparatus having the configuration described above.

<Preparation Step>

First, in a preparation step, an alkali metal fluoride, a polar aprotic solvent, and a glycol ether are charged into the reactor, the reactor is heated, and thus a suspension containing the alkali metal fluoride suspended in a mixed solvent is prepared in the reactor, for example. The temperature of the suspension inside the reactor is preferably maintained at 115° C. or higher until the point at which supply of 1-chloroheptafluorocyclopentene as a feedstock commences. Also note that the temperature of the suspension at the point at which feedstock supply commences is preferably 130° C. or lower. Setting the temperature of the suspension at the point at which feedstock supply commences as not lower than the lower limit set forth above can promote a fluorination reaction in a subsequent fluorination step. Moreover, setting the temperature of the suspension at the point at which the feedstock commences as not higher than the upper limit set forth above can inhibit concentration of 1-chloroheptafluorocyclopentene (feedstock) at the top of the rectification column installed at the top of the reactor, which is due to 1-chloroheptafluorocyclopentene having a low boiling point, and can improve the yield of octafluorocyclopentene.

<Fluorination Step Through to Recovery Step>

In a fluorination step, the suspension inside the reactor that is obtained in the preparation step is maintained at 85° C. or higher while 1-chloroheptafluorocyclopentene is supplied into the suspension as a feedstock and is fluorinated to obtain octafluorocyclopentene. More specifically, 1-chloroheptafluorocyclopentene used as a feedstock is first supplied into the reactor using a pump or the like. The supply rate of 1-chloroheptafluorocyclopentene is preferably within a range of 0.4 g/min to 0.7 g/min. When the supply rate is not less than the lower limit set forth above, the time required for the fluorination step can be shortened, and the manufacturing efficiency of octafluorocyclopentene can be further improved. Moreover, when the supply rate is not more than the upper limit set forth above, reduction of the temperature inside the reactor caused by addition of 1-chloroheptafluorocyclopentene can be effectively inhibited, and reduction of the rate of the fluorination reaction in the fluorination step can be effectively inhibited. This enables further improvement of the yield of octafluorocyclopentene.

It is not necessary to cool or heat the 1-chloroheptafluorocyclopentene that is supplied into the suspension as a feedstock. In other words, the 1-chloroheptafluorocyclopentene used as a feedstock may be supplied into the reactor at a temperature corresponding to room temperature or outdoor air temperature. However, it should be noted that the temperature of the 1-chloroheptafluorocyclopentene feedstock at the time of supply is preferably approximately 50° C. or lower from a viewpoint of inhibiting volatilization and enabling stable supply.

After the supply of 1-chloroheptafluorocyclopentene as a feedstock has commenced, withdrawal of product and trapping thereof in a cooled receiver is commenced approximately 30 minutes or more after the temperature at the top of the rectification column reaches 26° C. to 27° C. (recovery step). In this manner, octafluorocyclopentene that has been purified in the fluorination step can be recovered in the recovery step. During a period from when product withdrawal commences until the reaction time in the fluorination step elapses, withdrawal of product is continued, and the heating temperature of the reactor may be gradually increased depending on the temperature at the top of the rectification column and the state of refluxing. In this manner, the fluorination step and the recovery step may proceed concurrently from a point at which a certain time has elapsed after the start of the fluorination step.

The reaction time (required time) in the fluorination step depends on the size of the reactor and the scale on which the reaction is implemented, but is preferably 6 hours to 30 hours, and more preferably 7 hours to 15 hours. A reaction time that is too short leads to a poor conversion rate of 1-chloroheptafluorocyclopentene feedstock and reduced yield of octafluorocyclopentene, whereas a reaction time that is too long results in superfluous energy cost.

<Purification Step>

A purification step may optionally be implemented after the recovery step. In the purification step, the octafluorocyclopentene trapped in the receiver is subjected to a purification process such as distillation purification. In this manner, the purity of the product obtained in the fluorination step can be further increased.

EXAMPLES

The present disclosure is described in more detail below through examples. However, the scope of the present disclosure is not limited by the following examples. Note that pressures refer to gauge pressures. Moreover, the volumes of various solvents charged in preparation steps of the examples and comparative examples are volumes measured at 23° C. Furthermore, the yield of octafluorocyclopentene obtained in each example or comparative example was calculated as a ratio of the absolute yield of octafluorocyclopentene, as measured by gas chromatography analysis under the conditions shown below, relative to the additive amount of 1-chloroheptafluorocyclopentene as a feedstock.

<Gas Chromatography Analysis>

Gas chromatography analysis (GC analysis) was performed under the conditions shown below with respect to the reaction product obtained in each example or comparative example so as to analyze the content of octafluorocyclopentene in the reaction product.

Apparatus: HP-6890 (produced by Agilent Technologies, Inc.)

Column: Inert Cap-1 produced by GL Sciences Inc.; length: 60 m; internal diameter: 0.25 mm; film thickness: 1.5 μm Column temperature: Held at 40° C. for 10 minutes, subsequently raised at 20° C./min, and then held at 240° C. for 10 minutes
 Injection temperature: 200° C.
 Carrier gas: Nitrogen
 Split ratio: 100/1
 Detector: Flame ionization detector (FID)

Example 1

<Preparation Step>

A glass reactor of 500 mL in capacity that was equipped with a stirrer, a rectification column (produced by Toka Seiki Co., Ltd.; column length: 30 cm; packing: Heli Pack No. 1), and a feeding pump (QT-150 produced by Yamazen) was charged with spray dried potassium fluoride (33.7 g) as an alkali metal fluoride, 150 mL of dry N,N-dimethylformamide as a polar aprotic solvent, and 30 mL of diethylene glycol dimethyl ether (dried in advance using a 5 A molecular sieve) as a glycol ether having a higher boiling point than the polar aprotic solvent. The reactor was immersed in an oil bath, was heated to 120° C., and the contents thereof were stirred to obtain a suspension. The temperature of the suspension inside the reactor and the temperature at the top of the rectification column were each monitored by a thermocouple installed in a manner such as to enable measurement of the temperature of the suspension or the temperature at the top of the rectification column. A −10° C. coolant was circulated in a condenser of the rectification column.

<Fluorination Step Through to Recovery Step>

Once the temperature of the suspension inside the reactor reached 117° C., supply of 1-chloroheptafluorocyclopentene (supply temperature: 21° C.) into the reactor as a feedstock was commenced. The initial feedstock supply rate was set as 0.62 g/min and the supply rate was finely adjusted during the feedstock supply period while supplying the feedstock over 3.25 hours. The total supplied amount of feedstock was 114.5 g. During this period, the minimum temperature of the suspension inside the reactor was 90.4° C. After approximately 1.4 hours from the start of feedstock feeding, product withdrawal was commenced with a reflux ratio of 60 (temperature at top of rectification column: 26.6° C.). Thereafter, heating at 120° C. and product withdrawal with a reflux ratio of 60 were continued, and the oil bath temperature was raised in stages to 130° C. and 140° C. while observing the temperature at the top of the rectification column and the state of refluxing. The temperature at the top of the rectification column started to decrease after 6 hours from the start of feedstock supply. Therefore, the temperature of the oil bath was lowered to 120° C., an aspirator was connected to a distillation head of the rectification column, and the system was depressurized by a pressure of −0.09 MPa so as to recover holdup. The total amount of crude product that was recovered was 101.6 g. The content of octafluorocyclopentene (target product) in the crude product was determined from the results of gas chromatography analysis. Moreover, a ratio of the absolute yield of the obtained target product relative to the supplied amount of feedstock was calculated. The results are shown in Table 1.

Example 2

Operations were carried out in the same way as in Example 1 with the exception that diethylene glycol dimethyl ether used as the glycol ether was changed to 30 mL of diethylene glycol diethyl ether (dried in advance using a 5 A molecular sieve). Note that the temperature of the suspension at the point at which feedstock supply commenced, the total supplied amount of feedstock, and the minimum temperature of the suspension in the fluorination step were as shown in Table 1. Moreover, the total amount of crude product recovered through the recovery step was 100.9 g. The result for the yield of target product calculated in the same way as in Example 1 is shown in Table 1.

Example 3

Operations were carried out in the same way as in Example 1 with the exception that diethylene glycol dimethyl ether used as the glycol ether was changed to 30 mL of triethylene glycol dimethyl ether (dried in advance using a 5 A molecular sieve). Note that the temperature of the suspension at the point at which feedstock supply commenced, the total supplied amount of feedstock, and the minimum temperature of the suspension in the fluorination step were as shown in Table 1. Moreover, the total amount of crude product recovered through the recovery step was 102.1 g. The result for the yield of target product calculated in the same way as in Example 1 is shown in Table 1.

Example 4

Operations were carried out in the same way as in Example 1 with the exception that diethylene glycol dimethyl ether used as the glycol ether was changed to 45 mL of triethylene glycol dimethyl ether (dried in advance using a 5 A molecular sieve). Note that the temperature of the suspension at the point at which feedstock supply commenced, the total supplied amount of feedstock, and the minimum temperature of the suspension in the fluorination step were as shown in Table 1. Moreover, the total amount of crude product recovered through the recovery step was 101.3 g. The result for the yield of target product calculated in the same way as in Example 1 is shown in Table 1.

Example 5

Operations were carried out in the same way as in Example 1 with the exception that diethylene glycol dimethyl ether used as the glycol ether was changed to 30 mL of tetraethylene glycol dimethyl ether (dried in advance using a 5 A molecular sieve). Note that the temperature of the suspension at the point at which feedstock supply commenced, the total supplied amount of feedstock, and the minimum temperature of the suspension in the fluorination step were as shown in Table 1. Moreover, the total amount of crude product recovered through the recovery step was 102.9 g. The result for the yield of target product calculated in the same way as in Example 1 is shown in Table 1.

Example 6

Operations were carried out in the same way as in Example 1 with the exception that diethylene glycol dimethyl ether used as the glycol ether was changed to 30 mL of dipropylene glycol dimethyl ether (dried in advance using a 5 A molecular sieve). Note that the temperature of the suspension at the point at which feedstock supply commenced, the total supplied amount of feedstock, and the minimum temperature of the suspension in the fluorination step were as shown in Table 1. Moreover, the total amount of crude product recovered through the recovery step was 101.3 g. The result for the yield of target product calculated in the same way as in Example 1 is shown in Table 1.

Example 7

Operations were carried out in the same way as in Example 1 with the exception that dry N,N-dimethylformamide used as the polar aprotic solvent was changed to dry N,N-dimethylacetamide, and diethylene glycol dimethyl ether used as the glycol ether having a higher boiling point than the polar aprotic solvent was changed to triethylene glycol dimethyl ether (dried in advance using a 5 A molecular sieve). Note that the temperature of the suspension at the point at which feedstock supply commenced, the total supplied amount of feedstock, and the minimum temperature of the suspension in the fluorination step were as shown in Table 1. Moreover, at the point at which product withdrawal with a reflux ratio of 60 commenced after approximately 1.4 hours from the start of feedstock feeding, the temperature at the top of the rectification column was 26.1° C. Furthermore, the total amount of crude product recovered through the recovery step was 101.9 g. The result for the yield of target product calculated in the same way as in Example 1 is shown in Table 1.

Example 8

Operations were carried out in the same way as in Example 7 with the exception that triethylene glycol dimethyl ether used as the glycol ether was changed to 30 mL of dipropylene glycol dimethyl ether (dried in advance using a 5 A molecular sieve). Note that the temperature of the suspension at the point at which feedstock supply commenced, the total supplied amount of feedstock, and the minimum temperature of the suspension in the fluorination step were as shown in Table 1. Moreover, the total amount of crude product recovered through the recovery step was 101.7 g. The result for the yield of target product calculated in the same way as in Example 1 is shown in Table 1.

Comparative Example 1

Operations were carried out in the same way as in Example 1 with the exception that diethylene glycol dimethyl ether (glycol ether having a higher boiling point than the polar aprotic solvent) was not added. Note that the temperature of the suspension at the point at which feedstock supply commenced, the total supplied amount of feedstock, and the minimum temperature of the suspension in the fluorination step were as shown in Table 1. After approximately 2 hours from the start of product withdrawal, the temperature at the top of the rectification column increased to 30.7° C., and it was necessary to temporarily suspend product withdrawal. The total amount of crude product recovered through the recovery step was 101.4 g. The result for the yield of target product calculated in the same way as in Example 1 is shown in Table 1.

Comparative Example 2

Operations were carried out in the same way as in Example 7 with the exception that triethylene glycol dimethyl ether (glycol ether) was not added. Note that the temperature of the suspension at the point at which feedstock supply commenced, the total supplied amount of feedstock, and the minimum temperature of the suspension in the fluorination step were as shown in Table 1. After approximately 1.2 hours from the start of product withdrawal, the temperature at the top of the rectification column increased to 28.3° C., and it was necessary to temporarily suspend product withdrawal. The total amount of crude product recovered through the recovery step was 102.8 g. The result for the yield of target product calculated in the same way as in Example 1 is shown in Table 1.

Comparative Example 3

A reaction was carried out in the same way as in Example 1 with the exception that 30 mL of ethylene glycol dimethyl ether (dried in advance using a 5 A molecular sieve) having a lower boiling point (84° C.) than N,N-dimethylformamide (polar aprotic solvent) was used as the glycol ether. Note that the temperature of the suspension at the point at which feedstock supply commenced, the total supplied amount of feedstock, and the minimum temperature of the suspension in the fluorination step were as shown in Table 1. Approximately 20 minutes after feedstock supply commenced, reflux began in a condenser part of the rectification column and the temperature thereat was 53.6° C. It was clear that the 1-chloroheptafluorocyclopentene feedstock was vaporizing with almost no reaction thereof. Moreover, the temperature at the top of the column only decreased to 48.2° C. when the reaction was continued for 1.5 hours. Since this indicated that conversion to octafluorocyclopentene would be difficult even if the reaction were to be continued, the experiment was ended.

In Table 1:
"KF" indicates potassium fluoride;
"DMF" indicates N,N-dimethylformamide;
"DMA" indicates N,N-dimethylacetamide;
"Diglyme" indicates diethylene glycol dimethyl ether;
"Diglyet" indicates diethylene glycol diethyl ether;
"Triglyme" indicates triethylene glycol dimethyl ether;
"Tetraglyme" indicates tetraethylene glycol dimethyl ether;
"DPDME" indicates dipropylene glycol dimethyl ether; and
"Glyme" indicates ethylene glycol dimethyl ether.

TABLE 1

| | | | | Examples | | | | |
| --- | --- | --- | --- | --- | --- | --- | --- | --- |
| | | | | 1 | 2 | 3 | 4 | 5 |
| Fluorination step | Feedstock | 1-Chloroheptafluorocyclopentene (g) | | 114.5 | 114.3 | 114.4 | 114.4 | 114.4 |
| | Fluorinating agent | Alkali metal fluoride | Type | KF | KF | KF | KF | KF |
| | | | Amount (molar equivalents; feedstock basis) | 1.16 | 1.16 | 1.16 | 1.16 | 1.16 |
| | Mixed solvent | Polar aprotic solvent | Type | DMF | DMF | DMF | DMF | DMF |
| | | | Boiling point (° C.) | 153 | 153 | 153 | 153 | 153 |

TABLE 1-continued

|  |  |  |  | | | | | |
|---|---|---|---|---|---|---|---|---|
| | | | Amount (mL) | 150 | 150 | 150 | 150 | 150 |
| | | | Ratio (mL/g; feedstock basis) | 1.31 | 1.31 | 1.31 | 1.31 | 1.31 |
| | | Glycol ether | Type | Diglyme | Diglyet | Triglyme | Triglyme | Tetraglyme |
| | | | Boiling point (° C.) | 162 | 188 | 216 | 216 | 276 |
| | | | Amount (mL) | 30 | 30 | 30 | 45 | 30 |
| | | | Proportion (volume %; polar aprotic solvent basis) | 20 | 20 | 20 | 30 | 20 |
| | Suspension | | Temperature at point at which feedstock supply commences (° C.) | 117.0 | 115.1 | 115.0 | 115.5 | 115.4 |
| | | | Minimum temperature (° C.) | 90.4 | 90.0 | 93.4 | 90.2 | 91.5 |
| Evaluation | | | Yield (%) | 92.9 | 93.1 | 94.3 | 92.1 | 95.3 |

| | | | | Examples | | | Comparative Examples | | |
|---|---|---|---|---|---|---|---|---|---|
| | | | | 6 | 7 | 8 | 1 | 2 | 3 |
| Fluorination step | Feedstock | 1-Chloroheptafluorocyclopentene (g) | | 114.3 | 114.4 | 114.4 | 114.3 | 114.3 | 55.8 |
| | Fluorinating agent | Alkali metal fluoride | Type | KF | KF | KF | KF | KF | KF |
| | | | Amount (molar equivalents; feedstock basis) | 1.16 | 1.16 | 1.16 | 1.16 | 1.16 | 2.38 |
| | Mixed solvent | Polar aprotic solvent | Type | DMF | DMA | DMA | DMF | DMA | DMF |
| | | | Boiling point (° C.) | 153 | 165 | 165 | 153 | 165 | 153 |
| | | | Amount (mL) | 150 | 150 | 150 | 150 | 150 | 150 |
| | | | Ratio (mL/g; feedstock basis) | 1.31 | 1.31 | 1.31 | 1.31 | 1.31 | 2.69 |
| | | Glycol ether | Type | DPDME | Triglyme | DPDME | — | — | Glyme |
| | | | Boiling point (° C.) | 175 | 216 | 175 | — | — | 84 |
| | | | Amount (mL) | 30 | 30 | 30 | — | — | 30 |
| | | | Proportion (volume %; polar aprotic solvent basis) | 20 | 20 | 20 | — | — | 20 |
| | Suspension | | Temperature at point at which feedstock supply commences (° C.) | 115.4 | 116.4 | 115.2 | 115.2 | 116.1 | 93.7 |
| | | | Minimum temperature (° C.) | 89.1 | 94.4 | 94.9 | 82.6 | 84.0 | 72.2 |
| Evaluation | | | Yield (%) | 94.0 | 94.8 | 94.5 | 79.1 | 85.7 | — |

It can be seen from Table 1 that it was possible to sufficiently increase the yield of octafluorocyclopentene in Examples 1 to 8 in which a fluorination step of 1-chloroheptafluorocyclopentene was implemented under conditions such that the minimum temperature of a suspension obtained by suspending an alkali metal fluoride in a mixed solvent of a polar aprotic solvent and a glycol ether having a higher boiling point than the polar aprotic solvent did not drop below 85° C.

On the other hand, it can be seen that the yield could not be sufficiently increased in Comparative Examples 1 and 2 in which a suspension that did not contain a glycol ether was used.

It can also be seen that a fluorination step of 1-chloroheptafluorocyclopentene could not be caused to stably progress in Comparative Example 3 in which a suspension was used that had been prepared using a glycol ether that was a glycol ether having a lower boiling point than the polar aprotic solvent.

INDUSTRIAL APPLICABILITY

According to the present disclosure, it is possible to provide a manufacturing method that can sufficiently increase the yield of octafluorocyclopentene.

The invention claimed is:

1. A method of manufacturing octafluorocyclopentene by bringing 1-choroheptafluorocyclopentene into contact with an alkali metal fluoride to obtain octafluorocyclopentene, comprising:
    a fluorination step of maintaining, at 85° C. or higher, a suspension containing the alkali metal fluoride suspended in a mixed solvent including a polar aprotic solvent and a glycol ether having a higher boiling point than the polar aprotic solvent while supplying 1-choroheptafluoropentene into the suspension and performing fluorination thereof to obtain octafluorocyclopentene; and
    a recovery step of recovering the octafluorocyclopentene that is produced in the fluorination step.

2. The method of manufacturing octafluorocyclopentene according to claim 1, wherein a volume proportion of the glycol ether in the mixed solvent is not less than 10 volume % and not more than 30 volume % relative to 100 volume % of the polar aprotic solvent.

3. The method of manufacturing octafluorocyclopentene according to claim 1, wherein the polar aprotic solvent is N,N-dimethylformamide or N,N-dimethylacetamide.

4. The method of manufacturing octafluorocyclopentene according to claim 1, wherein the glycol ether is a dialkyl ether of polyethylene glycol or a dialkyl ether of polypropylene glycol.

5. The method of manufacturing octafluorocyclopentene according to claim 1, wherein the glycol ether includes at least one of diethylene glycol dimethyl ether, diethylene glycol diethyl ether, triethylene glycol dimethyl ether, tetraethylene glycol dimethyl ether, and dipropylene glycol dimethyl ether.

* * * * *